US010086661B2

(12) United States Patent
Tsujita

(10) Patent No.: US 10,086,661 B2
(45) Date of Patent: *Oct. 2, 2018

(54) TIRE CONDITION DETECTING APPARTUS

(71) Applicant: PACIFIC INDUSTRIAL CO., LTD., Ogaki-shi, Gifu-ken (JP)

(72) Inventor: Yasuhisa Tsujita, Motosu (JP)

(73) Assignee: PACIFIC INDUSTRIAL CO., LTD., Ogaki-Shi, Gifu-Ken (JP)

( * ) Notice: Subject to any disclaimer, the term of this patent is extended or adjusted under 35 U.S.C. 154(b) by 14 days.

This patent is subject to a terminal disclaimer.

(21) Appl. No.: 15/119,819

(22) PCT Filed: Sep. 17, 2015

(86) PCT No.: PCT/JP2015/076550
§ 371 (c)(1),
(2) Date: Aug. 19, 2016

(87) PCT Pub. No.: WO2017/046923
PCT Pub. Date: Mar. 23, 2017

(65) Prior Publication Data
US 2017/0267036 A1 Sep. 21, 2017

(51) Int. Cl.
B60C 23/02 (2006.01)
B60C 23/04 (2006.01)
(Continued)

(52) U.S. Cl.
CPC ........ B60C 23/0435 (2013.01); B60C 11/243 (2013.01); B60C 23/0454 (2013.01);
(Continued)

(58) Field of Classification Search
None
See application file for complete search history.

(56) References Cited

U.S. PATENT DOCUMENTS 6,408,690 B1 * 6/2002 Young ................ B60C 23/0408
73/146.5
2002/0039066 A1 * 4/2002 Fuller ................ B60C 23/0408
340/442
(Continued)

FOREIGN PATENT DOCUMENTS

JP 11326099 A 11/1999
JP 2003025818 A 1/2003
(Continued)

OTHER PUBLICATIONS

Communication date Dec. 15, 2017, Application No. 15881415.2-1760 / 3165384 PCT/JP2015076550, The extended European search report includes, pursuant to Rule 62 EPC, the supplementary European search report (Art. 153(7) EPC) and the European search opinion.

(Continued)

Primary Examiner — Andre Allen
(74) Attorney, Agent, or Firm — Cantor Colburn LLP

(57) ABSTRACT

A tire condition detecting apparatus includes a transmitting section, a receiving section, a control section, a property detecting section, and a battery, which is a power source for the apparatus. The control section operates in a control mode that is selected from a normal mode and a power saving mode. In the power saving mode, power consumption associated with reception of the wirelessly transmitted signal from the external device is less than that in the normal mode. When the amount of change in the electrical property of a valve stem detected by the property detecting section exceeds a reference change amount, the control section switches the control mode to the normal mode. The control section also switches the control mode to the power saving mode when a termination condition is met in the normal mode 6 Claims, 4 Drawing Sheets

(51) Int. Cl.
  *B60C 11/24* (2006.01)
  *G01N 27/22* (2006.01)
  *H04B 7/24* (2006.01)

(52) U.S. Cl.
  CPC ...... *B60C 23/0494* (2013.01); *B60C 23/0496* (2013.01); *G01N 27/22* (2013.01); *H04B 7/24* (2013.01); *Y02D 70/00* (2018.01); *Y02D 70/448* (2018.01)

(56) References Cited

U.S. PATENT DOCUMENTS

| | | | |
|---|---|---|---|
| 2003/0011472 A1 | 1/2003 | Itou et al. | |
| 2003/0080861 A1* | 5/2003 | Okubo | B60C 23/0416 340/442 |
| 2003/0090373 A1 | 5/2003 | Brgerhoff et al. | |
| 2003/0093197 A1 | 5/2003 | Bergerhoff et al. | |
| 2004/0046651 A1 | 3/2004 | Norimatsu | |
| 2005/0199328 A1* | 9/2005 | Schoenberger | B60C 23/0405 152/415 |
| 2006/0082451 A1* | 4/2006 | Shaw | B60C 23/0408 340/449 |
| 2006/0103240 A1 | 5/2006 | Naito et al. | |
| 2006/0220805 A1* | 10/2006 | Thomas | B60C 23/0416 340/426.33 |
| 2007/0125161 A1* | 6/2007 | Bryzek | B60C 23/0408 73/146.4 |
| 2012/0044064 A1 | 2/2012 | Maekawa et al. | |
| 2014/0150543 A1 | 6/2014 | Shima et al. | |
| 2017/0040911 A1* | 2/2017 | Tatarchuk | H01L 41/18 |
| 2017/0197481 A1* | 7/2017 | Peine | B60C 23/0486 |
| 2017/0227382 A1* | 8/2017 | Tsujita | G01D 5/244 |

FOREIGN PATENT DOCUMENTS

| | | |
|---|---|---|
| JP | 2004098835 A | 4/2004 |
| JP | 2006138156 A | 6/2006 |
| JP | 2011016462 A | 1/2011 |
| JP | 2012051499 A | 3/2012 |
| JP | 2012236556 A | 12/2012 |
| JP | 2014051249 A | 3/2014 |
| JP | 2015016786 A | 1/2015 |
| WO | 2015075494 A1 | 5/2015 |

OTHER PUBLICATIONS

Received an Office Action (Notification of Reason for Refusal) dated Mar. 13, 2018, during the prosecution of the corresponding Korean patent application 10-2016-7018774, 5 pages.
Office Action issued in Japanese Patent Application No. 2016-540717, dated Jul. 26, 2018; 7 pages (including English Translation of Notification of Reasons for Refusal).

\* cited by examiner

TIRE CONDITION DETECTING APPARTUS

TECHNICAL FIELD

The present invention relates to a tire condition detecting apparatus for detecting the condition of the tires of wheel assemblies.

BACKGROUND ART

Wireless type tire condition detecting apparatuses have been proposed. Such an apparatus is capable of detecting the condition of each of the tires attached to the wheels of the vehicle wheel assemblies. The tire of each wheel assembly of the vehicle incorporates a tire condition detecting apparatus, which detects the condition of the tire and wirelessly transmits a signal related to the detected tire condition. When a receiver receives each signal, a display in the passenger compartment displays information related to the condition of the corresponding tire as necessary. Also, since each tire condition detecting apparatus is attached to a wheel assembly, the apparatus incorporates a battery to supply power.

For example, the tire condition detecting apparatus disclosed in Patent Document 1 is capable of receiving wireless signals from external devices such as portable terminals. When confirming that the tire condition detecting apparatus is operating normally or that the tire air pressure is appropriate after replacement of the tire, the tire condition detecting apparatus transmits a signal related to the condition of the tire in response to reception of a request signal from an external device.

PRIOR ART DOCUMENT

Patent Document

Patent Document 1: Japanese Laid-Open Patent Publication No. 2006-138156

SUMMARY OF THE INVENTION

Problems that the Invention is to Solve

It is desired to reduce the power consumption to extend the life of the batteries incorporated in tire condition detecting apparatuses.

Accordingly, it is an objective of the present invention to provide a tire condition detecting apparatus that is configured to reduce power consumption.

Means for Solving the Problems

To achieve the foregoing objective and in accordance with one aspect of the present invention, a tire condition detecting apparatus is provided that is attached to a valve stem of a wheel assembly of a vehicle to be arranged in a tire of the wheel assembly. The apparatus includes a condition detecting section configured to detect a condition of the tire, a transmitting section configured to wirelessly transmit a signal containing information detected by the condition detecting section, a receiving section capable of receiving the signal wirelessly transmitted from an external device, a control section configured to control the transmitting section and the receiving section, a property detecting section configured to detect an electrical property of the valve stem, and a battery, which is a power source for the tire condition detecting apparatus. The control section is configured to operate in a control mode that is selected from a normal mode and a power saving mode. In the normal mode, the receiving section is maintained in a standby state, in which the receiving section is capable of receiving a wirelessly transmitted signal from the external device, and in the power saving mode, power consumption associated with reception of the wirelessly transmitted signal from the external device is less than that in the normal mode. The control section is configured to switch the control mode to the normal mode when an amount of change in the electrical property of the valve stem detected by the property detecting section exceeds a reference change amount. The control section is configured to switch the control mode to the power saving mode when a termination condition is met in the normal mode.

With this configuration, when the termination condition is met in the normal mode, the control mode is switched to the power saving mode, in which power consumption associated with reception of wirelessly transmitted signals from external devices is less than that in the normal mode. This reduces the power consumption associated with reception of wirelessly transmitted signals from external devices.

In the above described tire condition detecting apparatus, the property detecting section may be configured to detect a capacitance of the valve stem.

With this configuration, when the worker touches the valve stem after the tire is replaced, the control mode is switched to the normal mode if the amount of change in the capacitance of the valve stem exceeds the reference change amount.

In the above described tire condition detecting apparatus, the receiving section may be capable of receiving a signal of a frequency band of an ultra-high frequency.

With this configuration, signals of a frequency band of an ultra-high frequency can be received. The power consumption associated with signal reception is greater than in a case in which signals of radio waves in a frequency band of a very high frequency are received. However, by switching the control mode from the normal mode to the power saving mode, the receiving section is less frequently set to the standby state, in which the receiving section can receive signals. This reduces the power consumption associated with reception of wirelessly transmitted signals from external devices.

In the above described tire condition detecting apparatus, the termination condition may be met when any of the following conditions is met: a condition that the receiving section has received a wirelessly transmitted signal from the external device; a condition that a predetermined time has elapsed since the control mode was switched to the normal mode; and a condition that the vehicle has been detected to be moving.

With this configuration, wirelessly transmitted signals from external devices can be received. Also, the control mode can be switched from the normal mode to the power saving mode when the receiving section receives a wirelessly transmitted signal from an external device. This reduces the power consumption associated with reception of wirelessly transmitted signal from external devices.

When the predetermined time has elapsed since the control mode was switched to the normal mode, the control mode can be switched from the normal mode to the power saving mode, so that the receiver is less frequently set to the standby state. This reduces the power consumption associated with reception of the wirelessly transmitted signal from the external device.

Also, when the vehicle is detected to be moving, the receiving section has a tendency of receiving wirelessly transmitted signals from external devices less frequently than in the case in which a stopping state of the vehicle is detected. Thus, when the vehicle is detected to be moving, that is, when wirelessly transmitted signals from external devices are less frequently received, the control mode is switched from the normal mode to the power saving mode so that the receiving section is less frequently set to the standby state. This reduces the power consumption associated with reception of wirelessly transmitted signals from external devices.

In the above described tire condition detecting apparatus, the control section may be configured not to execute, in the normal mode, a process of identifying the amount of change in the electrical property of the valve stem.

In the above described tire condition detecting apparatus, the control section may be configured to execute the process of identifying the amount of change in the electrical property of the valve stem when the vehicle is in a stopped state. Also, the control section may be configured not to execute the process of identifying the amount of change in the electrical property of the valve stem when the vehicle is moving.

EFFECTS OF THE INVENTION

The present invention reduces the power consumption of the tire condition detecting apparatus.

MODES FOR CARRYING OUT THE INVENTION

One embodiment of the present invention will now be described.

Figure 1:
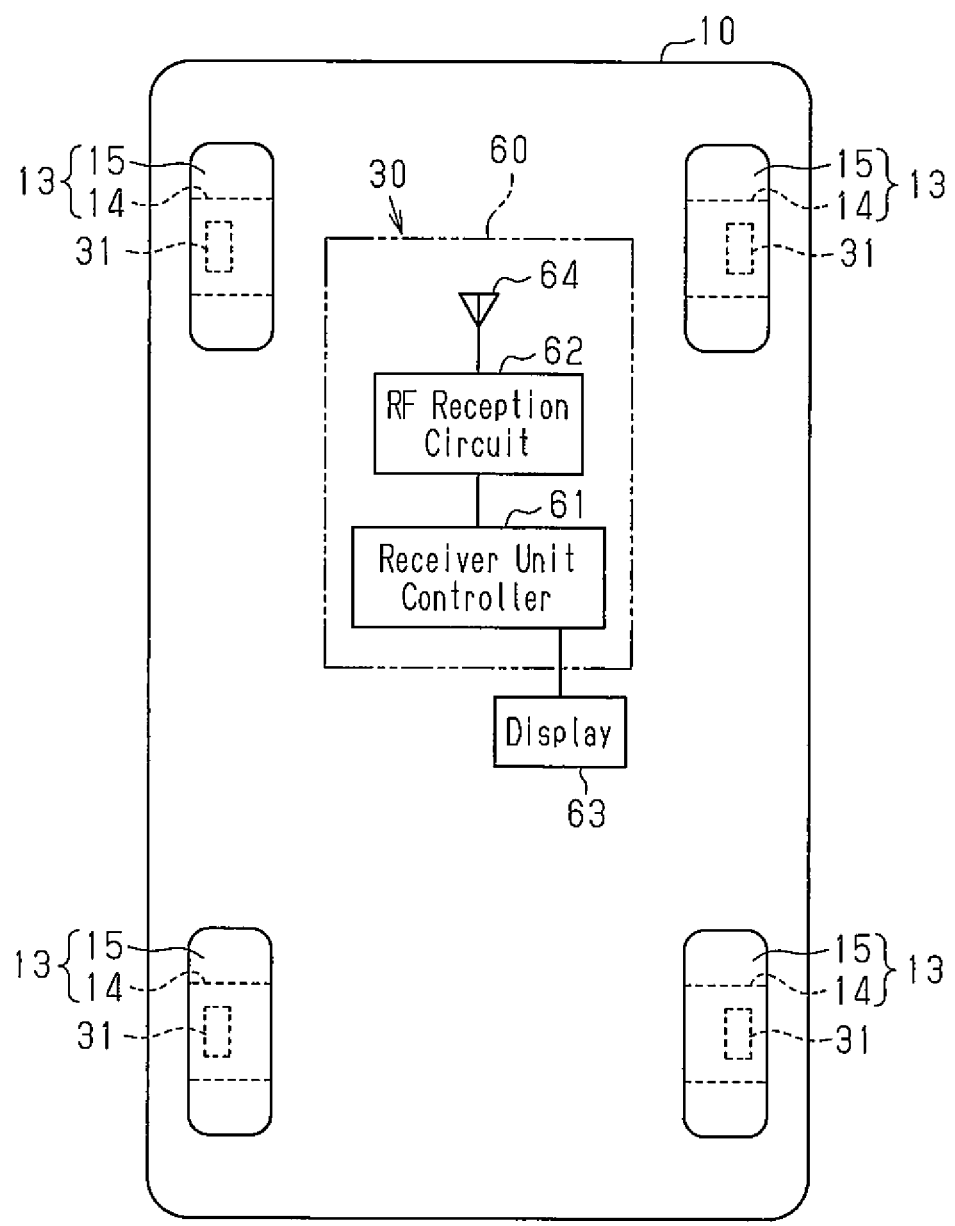
FIG. 1 is a schematic diagram illustrating a vehicle on which sensor units according to one embodiment are mounted.

As shown in FIG. 1, a vehicle 10 has four wheel assemblies 13, and a tire condition monitoring apparatus 30. Each wheel assembly 13 includes a vehicle wheel 14 and a tire 15 attached to the vehicle wheel 14.

The tire condition monitoring apparatus 30 includes sensor units 31, which are attached to the respective wheel assemblies 13, and a receiver unit 60, which is arranged in the body of the vehicle 10.

Figure 2:
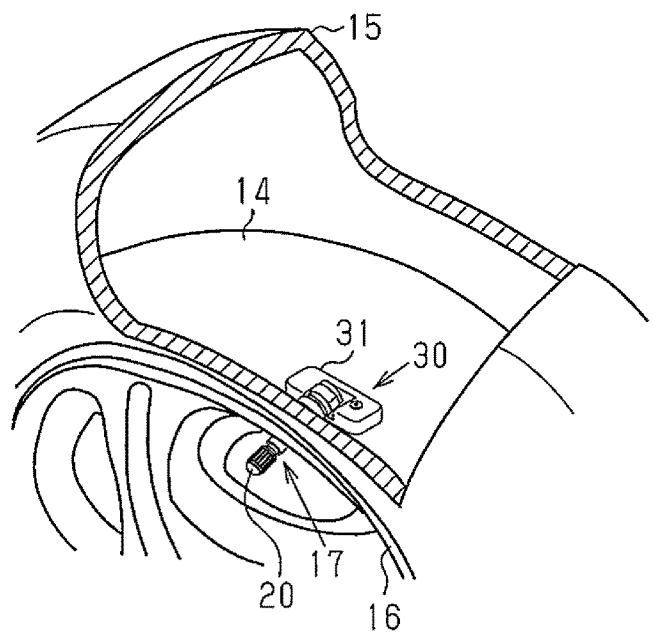
FIG. 2 is a perspective view illustrating a state in which a tire valve of the embodiment is attached to a rim.

As shown in FIG. 2, each wheel 14 has a rim 16, to which a tire valve 17 is attached. A sensor unit 31 is attached to and integrated with the tire valve 17 to be arranged in the tire 15 attached to the vehicle wheel 14.

Figure 3:
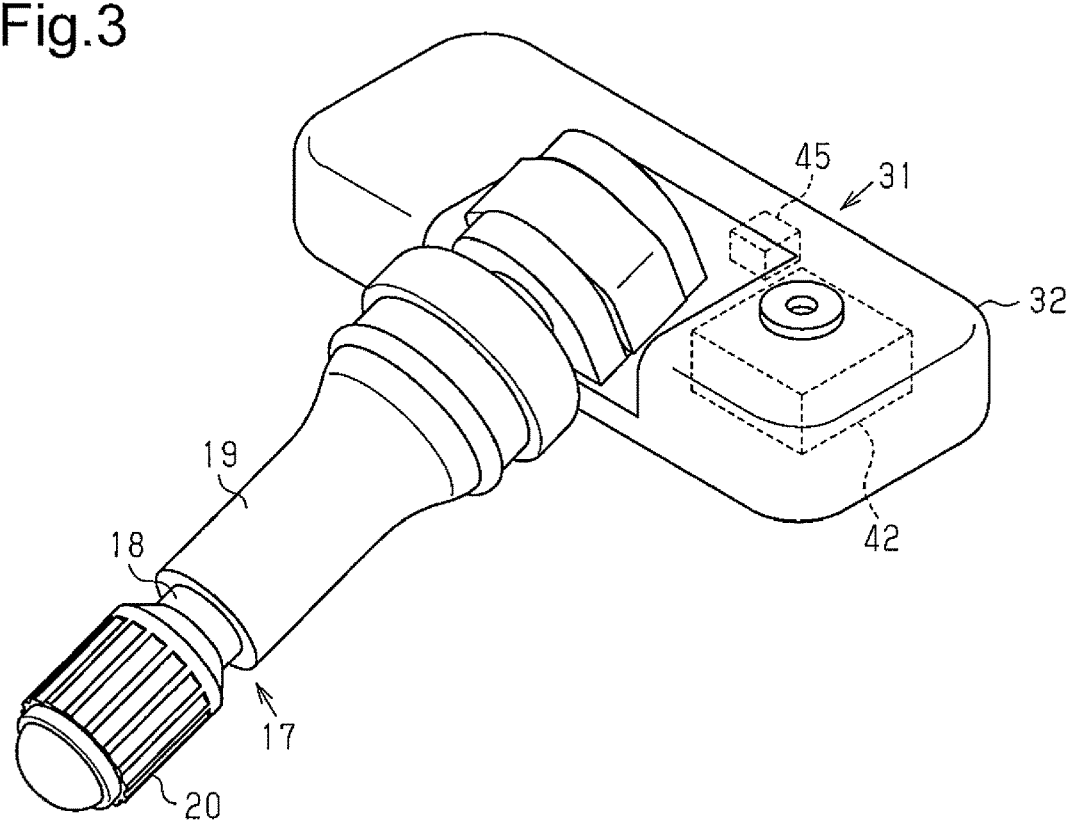
FIG. 3 is a perspective view showing the tire valve and the sensor unit of the embodiment.

As shown in FIG. 3, the tire valve 17 includes a cylindrical metal valve stem 18 and a rubber body 19, which is attached to the outer circumferential surface of the valve stem 18. The valve stem 18 has an introduction passage (not shown). A valve mechanism (not shown) is incorporated in the distal portion of the valve stem 18, and a cap 20 is attached to the distal end of the valve stem 18.

A housing 32 of the sensor unit 31 accommodates electronic components such as a pressure sensor 42 and a capacitance sensor 45, a battery, and an antenna. The pressure sensor 42 detects the pressure of the tire 15. The capacitance sensor 45 is electrically connected to the tire valve 17 to detect the capacitance of the tire valve 17.

Figure 4:
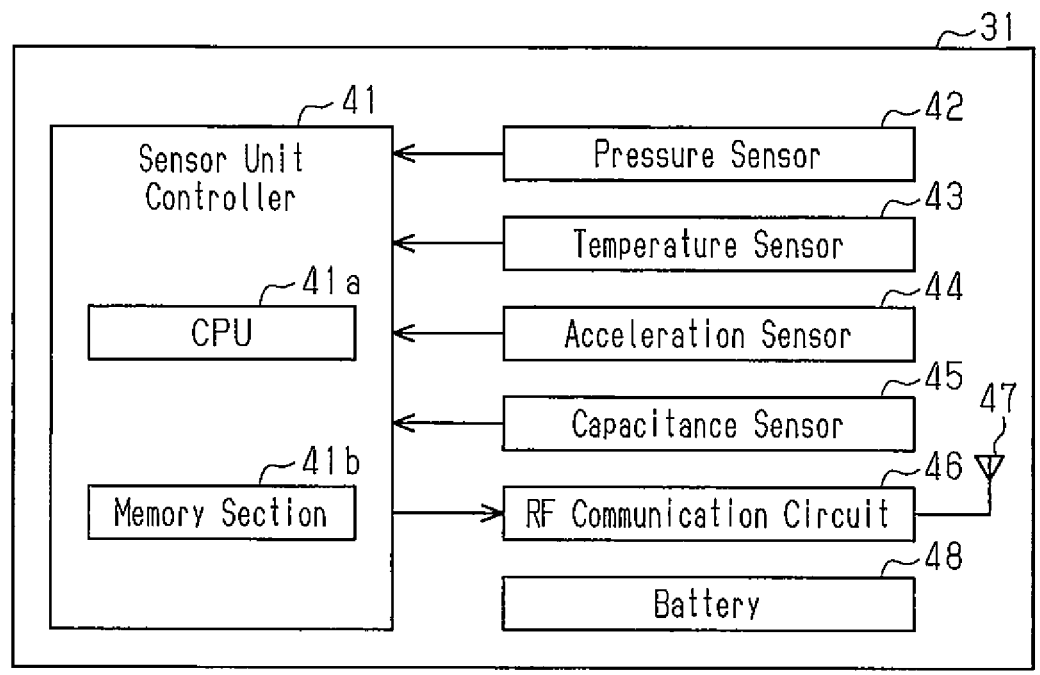
FIG. 4 is a block diagram illustrating the electrical configuration of the sensor unit of the embodiment.

As shown in FIG. 4, each sensor unit 31 includes a sensor unit controller 41, a pressure sensor 42, a temperature sensor 43, an acceleration sensor 44, a capacitance sensor 45, an RF communication circuit 46, an RF antenna 47, and a battery 48. The sensor unit 31 is driven by power supplied by the battery 48.

The pressure sensor 42, which functions as a condition detecting section, detects the air pressure in the tire 15. The temperature sensor 43, which functions as a condition detecting section, detects the temperature in the tire 15. That is, the pressure sensor 42 and the temperature sensor 43 detect the condition of the tire 15. The acceleration sensor 44, rotates integrally with the wheel assembly 13 to detect the acceleration acting on the acceleration sensor 44. The capacitance sensor 45, which is a property detecting section, detects the capacitance of the valve stem 18 of the tire valve 17 in the wheel assembly 13. The RF communication circuit 46, which functions as a transmitting section and a receiving section, transmits and receives signals via the RF antenna 47 by using radio waves in a frequency band of an ultra-high frequency (2.4 GHz in the present embodiment). In the present embodiment, the RF communication circuit 46 can be switched between a standby state and a quiescent state. In the standby state, the RF communication circuit 46 is capable of receiving a signal (a trigger signal), which is wirelessly transmitted from an external device (for example, the receiver unit 60 or a trigger signal transmitter that can be carried by the worker). In the quiescent state, the RF communication circuit 46 cannot receive signals wirelessly transmitted from external devices.

The sensor unit controller 41 is a control circuit or a processor, which is constituted by a microcomputer having a CPU 41a, a memory section 41b (such as a RAM and a ROM), and an input-output port. The memory section 41b of the sensor unit controller 41 stores programs for controlling operation of the sensor unit 31 in an integrated manner. In the memory section 41b, an ID code is registered, which is identification information unique to each sensor unit 31. The ID code is information used to identify each sensor unit 31 at the receiver unit 60. The sensor unit controller 41 functions as a control section.

The sensor unit controller 41, specifically, the CPU 41a, obtains, at a predetermined obtainment interval, the tire air pressure detected by the pressure sensor 42, the tire internal temperature detected by the temperature sensor 43, and the acceleration (gravitational acceleration) detected by the acceleration sensor 44. The sensor unit 31, which includes the sensor unit controller 41, the pressure sensor 42, and the temperature sensor 43, functions a tire condition detecting apparatus, which is attached to the valve stem 18 to be arranged in the tire 15.

The sensor unit controller 41 is capable of identifying the acceleration acting on the sensor unit 31, specifically, the acceleration acting on the acceleration sensor 44 based on an acceleration signal from the acceleration sensor 44. Also, the sensor unit controller 41 is capable of determining whether the vehicle 10 is in a stopped state or moving based on the acceleration signal from the acceleration sensor 44. For example, the sensor unit controller 41 determines that the vehicle 10 is moving when the acceleration detected by the acceleration sensor 44 changes in a predetermined range (for example, a range from −1G to +1G).

When a predetermined output condition is met, the sensor unit controller 41 outputs, to the RF communication circuit 46, transmission data that contains the tire air pressure data, the tire internal temperature data, and the ID code. The RF communication circuit 46 generates a transmission signal by modulating the transmission data output from the sensor unit controller 41, and wirelessly transmits the transmission signal from the RF antenna 47. In the present embodiment, the output condition is met each time a predetermined time elapses. That is, the sensor unit controller 41 executes transmission each time the predetermined time elapses. The output condition may include determination that the tire air pressure or the tire internal temperature is abnormal.

When determining that the vehicle 10 is in a stopped state and that the RF communication circuit 46 is controlled to be in the quiescent state, the sensor unit controller 41 identifies the capacitance of the valve stem 18 of the tire valve 17 based on a signal from the capacitance sensor 45 and stores capacitance data indicating the identified capacitance in the memory section 41b. In the present embodiment, the sensor unit controller 41 performs a series of processes for identifying the capacitance and storing the capacitance data for approximately 1 ms at a predetermined interval (for example, 1 s).

The sensor unit controller 41 determines whether the amount of change in the identified capacitance of the valve stem 18 has exceeded a predetermined reference change amount. When the tire 15 is replaced, the worker touches the valve stem 18 of the tire valve 17. Thus, the reference change amount is defined as the amount of change in the capacitance at which it is possible to assume that the worker has touched the valve stem 18.

When determining that the vehicle 10 is moving or that the RF communication circuit 46 is controlled to be in the standby state, the sensor unit controller 41 does not execute the process for identifying the capacitance of the valve stem 18.

As shown in FIG. 1, the receiver unit 60 includes a receiver unit controller 61, an RF reception circuit 62, and a reception antenna 64. A display 63 is connected to the receiver unit controller 61. The receiver unit controller 61 is a processor, which is constituted by a microcomputer including a CPU and a memory section (such as a ROM and a RAM). The memory section stores programs for controlling operation of the receiver unit 60 in an integrated manner. The RF reception circuit 62 demodulates signals delivered from the sensor units 31 via the reception antenna 64 and delivers the demodulated signals to the receiver unit controller 61.

Based on a signal demodulated by the RF reception circuit 62, the receiver unit controller 61 identifies the condition of the tire 15 (the tire air pressure and the tire internal temperature) that corresponds to the sensor unit 31 that is the source of the signal. The receiver unit controller 61 causes the display 63 to show information regarding the conditions of the tires 15.

In the present embodiment, the sensor unit controller 41 is capable of setting, as the control mode, either one of a normal mode and a power saving mode, in which power consumption associated with reception of wirelessly transmitted signals from external devices is reduced compared to that in the normal mode. The sensor unit controller 41 sets the control mode by setting, as a control mode flag assigned to the memory section 41b, either a value indicating the normal mode or a value indicating the power saving mode.

In the present embodiment, the sensor unit controller 41 sets the RF communication circuit 46 to the standby state in the normal mode. In contrast, the sensor unit controller 41 sets the RF communication circuit 46 to the quiescent state in the power saving mode.

Figure 5:
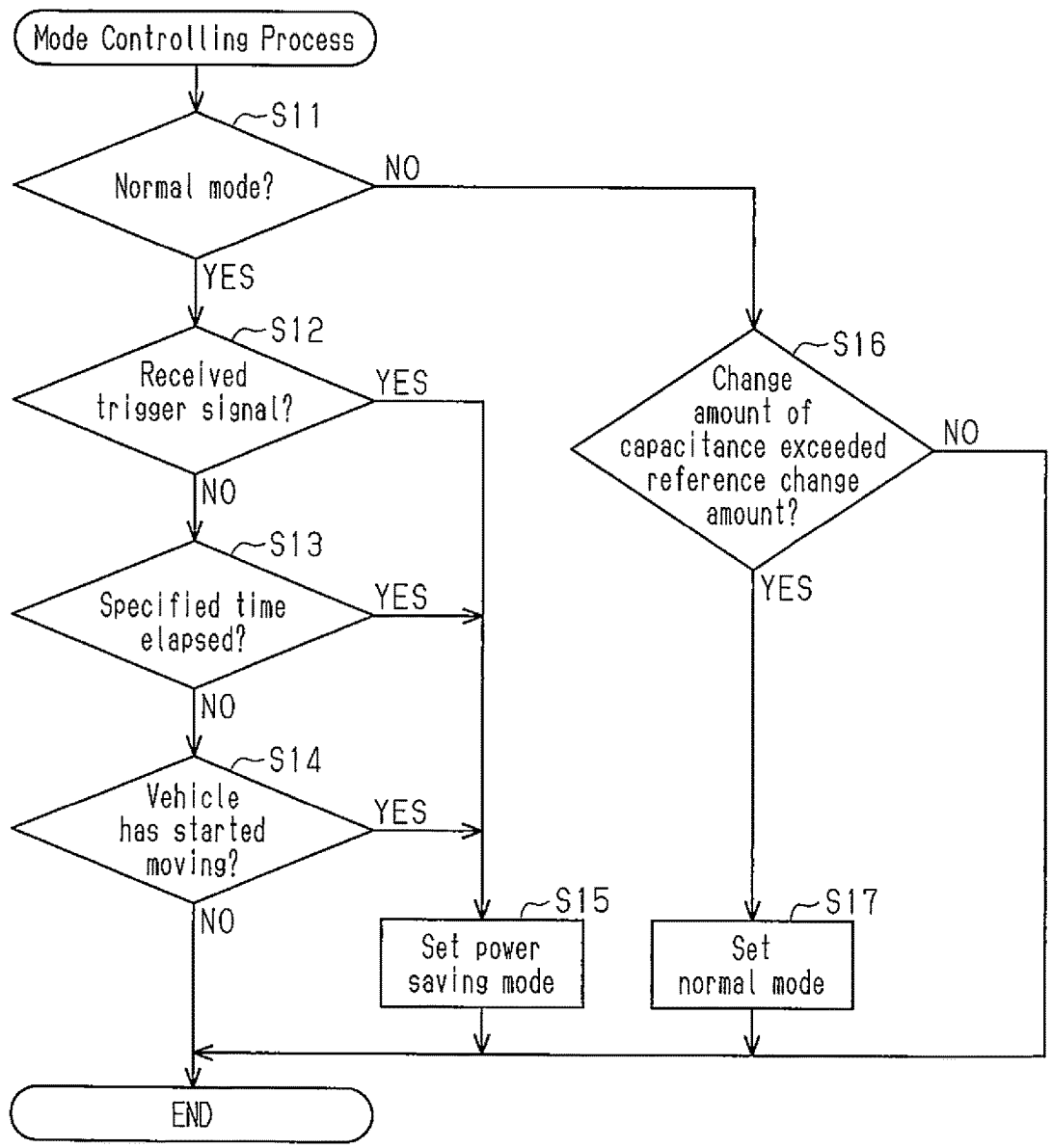
FIG. 5 is a flowchart showing a mode controlling process of the embodiment.

With reference to FIG. 5, a mode controlling process, which is executed by each sensor unit controller 41 at a predetermined interval, will now be described.

First, as shown in FIG. 5, the sensor unit controller 41 reads out the value of the control mode flag, which has been assigned to the memory section 41b. Based on the value, the sensor unit controller 41 determines whether the control mode is the normal mode (step S11). If it is determined that the control mode is the normal mode, the sensor unit controller 41 determines whether the RF communication circuit 46 has received a trigger signal (step S12). In the present embodiment, the trigger signal is a control signal transmitted from an external device to confirm that the sensor unit 31 is operating normally or that the tire condition is appropriate after replacement of the tire, or to set an ID code for the sensor unit 31. If it is determined that the RF communication circuit 46 has received a trigger signal, the sensor unit controller 41 executes the process in accordance with control information contained in the trigger signal and sets the control mode flag assigned to the memory section 41b to a value indicating the power saving mode, thereby setting the control mode to the power saving mode (step S15).

If it is not determined that the RF communication circuit 46 has received any trigger signals, the sensor unit controller 41 determines whether a specified time has elapsed since the control mode was set to the normal mode (step S13). If it is determined that the specified time has elapsed since the control mode was set to the normal mode, the sensor unit controller 41 sets the control mode flag assigned to the memory section 41b to a value indicating the power saving mode, thereby setting the control mode to the power saving mode (step S15).

If it is determined that the specified time has not elapsed since the control mode was set to the normal mode, the sensor unit controller 41 determines whether the vehicle 10 is moving (step S14). If it is determined that the vehicle 10 is moving, the sensor unit controller 41 sets the control mode flag assigned to the memory section 41b to a value indicating the power saving mode, thereby setting the control mode to the power saving mode (step S15). If it is determined that the vehicle 10 is not moving, the sensor unit controller 41 ends the mode controlling process without executing step S15.

If it is determined that the control mode is not the normal mode (that is, if the control mode is determined to be the power saving mode), the sensor unit controller 41 determines whether the amount of change in the capacitance has exceeded a reference change amount (step S16). If it is determined that the change amount of the capacitance has exceeded the reference change amount, the sensor unit controller 41 sets the control mode flag assigned to the memory section 41b to a value indicating the normal mode, thereby setting the control mode to the normal mode (step S17). If it is determined that the change amount of the capacitance has not exceeded the reference change amount in the power saving mode, the sensor unit controller 41 ends the mode controlling process without executing step S15.

The initiation condition for the normal mode (that is, the termination condition for the power saving mode) is met when the change amount of the capacitance of the valve stem 18 exceeds the reference change amount. In contrast, the termination condition for the normal mode (that is, the initiation condition for the power saving mode) is met when at least one of the following condition is met: the RF communication circuit 46 has received a trigger signal in the normal mode; the specified time has elapsed since the control mode was set to the normal mode; and the vehicle 10 is moving.

Operation of each sensor unit 31 according to the present embodiment will now be described.

In the normal mode, the RF communication circuit 46 of the sensor unit 31 is controlled to be in the standby state, in which the RF communication circuit 46 is capable of receiving wirelessly transmitted signals from external devices. In contrast, the RF communication circuit 46 is maintained in the quiescent state, in which the RF communication circuit 46 cannot receive wirelessly transmitted signals from external devices. When the vehicle 10 is moving or the RF communication circuit 46 is controlled to be in the standby state, the process for identifying the capacitance of the valve stem 18 is not executed. When the vehicle 10 is in a stopped state and the RF communication circuit 46 is controlled to be in the quiescent state, the process for identifying the capacitance of the valve stem 18 is executed.

The control mode is switched from the normal mode to the power saving mode when any one of the following condition is met: the RF communication circuit 46 has received a trigger signal in the normal mode; the specified time has elapsed since the control mode was set to the normal mode; and the vehicle 10 is moving. When the amount of change in the capacitance of the valve stem 18 has exceeded the reference change amount in the power saving mode, it is assumed that a worker has touched the valve stem 18 during tire replacement. In this case, the control mode is switched to the normal mode.

The above described embodiment has the following advantages.

(1) When the termination condition is met in the normal mode, the control mode is switched to the power saving mode, in which power consumption associated with reception of wirelessly transmitted signals from external devices is less than that in the normal mode. This reduces the power consumption associated with reception of wirelessly transmitted signals from external drives.

(2) In the power saving mode, the control mode is switched to the normal mode when the worker touches the valve stem 18 during replacement of the tire 15 and the amount of change in the capacitance of the valve stem 18 exceeds the reference change amount. Accordingly, the RF communication circuit 46 is switched to the standby state, in which the RF communication circuit 46 can receive wirelessly transmitted signals from external devices.

(3) The RF communication circuit 46 uses radio waves in a frequency band of an ultra-high frequency. In this case, the power consumption associated with signal reception is greater than in a case in which radio waves in a frequency band of a very high frequency are used. However, by switching the control mode to the power saving mode, the RF communication circuit 46 is less frequently set to the standby state, in which the RF communication circuit 46 can receive signals. This reduces the power consumption associated with reception of wirelessly transmitted signals from external devices.

(4) In the normal mode, the RF communication circuit 46 is maintained in the standby mode to be able to receive the trigger signal. When the RF communication circuit 46 receives the trigger signal, the control mode can be switched from the normal mode to the power saving mode. This reduces the power consumption associated with reception of wirelessly transmitted signals from external devices.

(5) When the predetermined time has elapsed since the control mode was switched to the normal mode, the control mode can be switched from the normal mode to the power saving mode, so that the RF communication circuit 46 is less frequently set to the standby state. This reduces the power consumption associated with reception of the wirelessly transmitted signal from the external device.

(6) When the vehicle 10 is moving, the RF communication circuit 46 tends to receive trigger signals less frequently than when the vehicle 10 is in a stopped state. Thus, when the vehicle 10 is detected to be moving, that is, when trigger signals are less frequently received, the control mode is switched from the normal mode to the power saving mode so that the RF communication circuit 46 is less frequently set to the standby state. This reduces the power consumption associated with reception of wirelessly transmitted signals from external devices.

(7) Since the tires 15 are replaced when the vehicle 10 is in a stopped state, the control mode can be switched to the normal mode by executing the process of identifying the capacitance of the valve stems 18 in a stopped state of the vehicle 10. Since tire replacement is never performed when the vehicle 10 is moving, no identification of the capacitances of the valve stems 18 is executed when the vehicle 10 is moving. The power consumption is reduced, accordingly.

(8) Since the RF communication circuit 46 has already been in the standby state when the control mode is the normal mode, no identification of the capacitances of the valve stems 18. The power consumption is reduced, accordingly.

The embodiment may be modified as follows.

The initiation condition of the normal mode may be different from that in the above illustrated embodiment. For example, the initiation condition of the normal mode may be met when a predetermined time has elapsed since the change amount of the capacitance of the valve stem 18 exceeded the reference change amount.

The sensor unit 31 may control the RF communication circuit 46 to be in the standby state as long as the power consumption in the power saving mode is less than that in the normal mode. Specific examples include the following configuration. That is, in the normal mode, the RF communication circuit 46 is controlled to be in a first standby state, in which the RF communication circuit 46 is capable of receiving wirelessly transmitted signals from external devices at a first specified interval. In the power saving mode, the RF communication circuit 46 is controlled to be in a second standby state, in which the RF communication circuit 46 is capable of receiving wirelessly transmitted signals from external devices at a second specified interval, which is longer than the first specified interval.

Each sensor unit 31 may execute determination regarding the capacitance of the corresponding valve stem 18 while the vehicle 10 is moving. That is, the sensor unit 31 may execute a process of determining the capacitance of the valve stem 18 regardless of whether the vehicle is in a stopped state or is moving.

The sensor unit 31 may execute determination regarding the capacitance of the corresponding valve stem 18 in the normal mode (the standby state of the RF communication circuit 46). That is, the process of determining the capacitance of the valve stem 18 may be performed regardless of the control mode.

The transmission circuit and the reception circuit may be separately provided, and the transmission circuit and the reception circuit use different frequency bands.

Each sensor unit 31 transmits signals using radio waves in a frequency band of an ultra-high frequency. However, each sensor unit 31 may transmit signals using radio waves in a frequency band of a frequency other than an ultra-high frequency.

Each sensor unit 31 may switch the control mode to the normal mode in response to the measurement result of the complex impedance including an inductor and a resistance value. That is, it suffices if the electrical property of the tire valve 17 can be detected so that it can be assumed that the tire valve 17 has been touched at replacement of the tire 15.

The termination condition of the normal mode may be met in accordance with factors other than reception of a trigger signal, lapse of the specified time, and moving of the vehicle 10. Alternatively, the termination condition of the normal mode may be met in accordance with a combination of these factors.

Each sensor unit 31 detects, as the condition of the tire, the air pressure and the temperature in the tire. However, each sensor unit 31 may detect either one of these parameters. Alternatively, each sensor unit 31 may detect other parameters such as the wear of the tire.

The sensor units 31 do not necessarily need to be employed in the tires of a four-wheeled vehicle, but may be employed in the tires of a vehicle having one to three wheels or five or more wheels.

DESCRIPTION OF THE REFERENCE NUMERALS

10 . . . Vehicle, 13 . . . Wheel Assembly, 14 . . . Vehicle Wheel, 15 . . . Tire, 17 . . . Tire Valve, 18 . . . Valve Stem, 30 . . . Tire Condition Monitoring Apparatus, 31 . . . Sensor Unit, 41 . . . Sensor Unit Controller, 42 . . . Pressure Sensor, 43 . . . Temperature Sensor, 44 . . . Acceleration Sensor, 45 . . . Capacitance Sensor, 46 . . . RF Communication Circuit, 48 . . . Battery, 60 . . . Receiver Unit.

What is claimed is:

1. A tire condition detecting apparatus, which is attached to a valve stem of a wheel assembly of a vehicle to be arranged in a tire of the wheel assembly, the apparatus comprising:
   a condition detecting section configured to detect a condition of the tire;
   a transmitting section configured to wirelessly transmit a signal containing information detected by the condition detecting section;
   a receiving section configured to receive a signal wirelessly transmitted from an external device;
   a control section configured to control the transmitting section and the receiving section;
   a property detecting section configured to detect an electrical property of the valve stem; and
   a battery, which is a power source for the tire condition detecting apparatus, wherein
   the control section is configured to operate in a control mode that is selected from a normal mode and a power saving mode, wherein, in the normal mode, the receiving section is maintained in a standby state, in which the receiving section is capable of receiving a wirelessly transmitted signal from the external device, and in the power saving mode, power consumption associated with reception of the wirelessly transmitted signal from the external device is less than that in the normal mode,
   the control section is configured to switch the control mode to the normal mode when an amount of change in the electrical property of the valve stem detected by the property detecting section exceeds a reference change amount, and
   the control section is configured to switch the control mode to the power saving mode when a termination condition is met in the normal mode.

2. The tire condition detecting apparatus according to claim 1, wherein the property detecting section is configured to detect a capacitance of the valve stem.

3. The tire condition detecting apparatus according to claim 1, wherein the receiving section is configured to receive a signal of a frequency band of an ultra-high frequency.

4. The tire condition detecting apparatus according to claim 1, wherein the termination condition is met when any of the following conditions is met:
   a condition that the receiving section has received a wirelessly transmitted signal from the external device;
   a condition that a predetermined time has elapsed since the control mode was switched to the normal mode; and
   a condition that the vehicle has been detected to be moving.

5. The tire condition detecting apparatus according to claim 1, wherein the control section is configured not to execute, in the normal mode, a process of identifying the amount of change in the electrical property of the valve stem.

6. The tire condition detecting apparatus according to claim 1, wherein
   the control section is configured to execute the process of identifying the amount of change in the electrical property of the valve stem when the vehicle is in a stopped state, and
   the control section is configured not to execute the process of identifying the amount of change in the electrical property of the valve stem when the vehicle is moving.

* * * * *